(12) United States Patent
Coulton et al.

(10) Patent No.: US 6,596,730 B1
(45) Date of Patent: Jul. 22, 2003

(54) PHENYL UREA AND PHENYL THIOUREA DERIVATIVES

(75) Inventors: Steven Coulton, Horsham (GB); Amanda Johns, St Albans (GB); Roderick Alan Porter, Ashwell (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/913,228

(22) PCT Filed: Feb. 10, 2000

(86) PCT No.: PCT/EP00/01142
§ 371 (c)(1),
(2), (4) Date: Dec. 5, 2001

(87) PCT Pub. No.: WO00/47580
PCT Pub. Date: Aug. 17, 2000

(30) Foreign Application Priority Data

Feb. 12, 1999 (GB) ............................................ 9903241
Nov. 8, 1999 (GB) ............................................ 9926441

(51) Int. Cl.[7] ................ A61K 31/4375; A61K 31/435; C07D 471/04; A61P 25/00
(52) U.S. Cl. ....................................... 514/300; 546/122
(58) Field of Search ........................... 546/122; 514/300

(56) References Cited

FOREIGN PATENT DOCUMENTS

| WO | WO 94/18170 | 8/1994 |
| WO | WO 99/09024 | 2/1999 |
| WO | WO 99/58533 | 11/1999 |

OTHER PUBLICATIONS

Austin, et al., "Pharmacokinetics of the Novel, High–Affinity and Selective Dopamine D3 Receptor Antagonist SB–277011 in Rat, Dog and Monkey: In Vitro/In Vivo Correlation and the Role of Aldehyde Oxidase", *Xenobiotica*, 31(8/9):677–686 (2001).

*Primary Examiner*—Evelyn Mei Huang
(74) *Attorney, Agent, or Firm*—Kathryn L. Sieburth; Mary McCarthy; Charles M. Kinzig

(57) ABSTRACT

Compounds of formula (I):

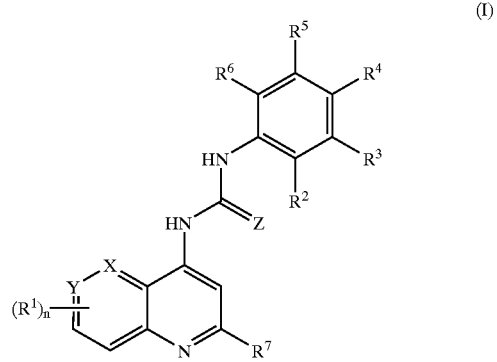

in which:
  one of X and Y is N and the other is CH;
  Z represents oxygen or sulfur;
  and $R^1$ to $R^7$ represent various substituent groups;
and pharmaceutically acceptable salts thereof.

3 Claims, No Drawings

PHENYL UREA AND PHENYL THIOUREA DERIVATIVES

This application is a 371 of PCT/EP00/01142, filed on Feb. 10, 2000.

This invention relates to phenyl urea and phenyl thiourea derivatives and their use as pharmaceuticals.

Many medically significant biological processes are mediated by proteins participating in signal transduction pathways that involve G-proteins and/or second messengers.

Polypeptides and polynucleotides encoding the human 7-transmembrane G-protein coupled neuropeptide receptor, orexin-1 (HFGAN72), have been identified and are disclosed in EP-A-875565, EP-A-875566 and WO 96/34877. Polypeptides and polynucleotides encoding a second human orexin receptor, orexin-2 (HFGANP), have been identified and are disclosed in EP-A-893498.

Polypeptides and polynucleotides encoding polypeptides which are ligands for the orexin-1 receptor, e.g. orexin-A (Lig72A) are disclosed in EP-A-849361.

Orexin receptors are found in the mammalian host and may be responsible for many biological functions, including pathologies including, but not limited to, depression; anxiety; addictions; obsessive compulsive disorder; affective neurosis/disorder; depressive neurosis/disorder; anxiety neurosis; dysthymic disorder; behaviour disorder; mood disorder; sexual dysfunction; psychosexual dysfunction; sex disorder; sexual disorder; schizophrenia; manic depression; delirium; dementia; severe mental retardation and dyskinesias such as Huntington's disease and Gilles de la Tourett's syndrome; disturbed biological and circadian rhythms; feeding disorders, such as anorexia, bulimia, cachexia, and obesity; diabetes; appetite/taste disorders; vomiting/nausea; asthma; cancer; Parkinison's disease; Cushing's syndrome/disease; basophil adenoma; prolactinoma; hyperprolactinemia; hypopituitarism; hypophysis tumor/adenoma; hypothalamic diseases; Froehlich's syndrome; adrenohypophysis disease; hypophysis disease; hypophysis tumor/adenoma; pituitary growth hormone; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; disturbed biological and circadian rhythms; and sleep disturbances associated with such diseases as neurological disorders, neuropathic pain and restless leg syndrome, heart and lung diseases; acute and congestive heart failure; hypotension; hypertension; urinary retention; osteoporosis; angina pectoris; myocardial infarction; ischaemic or haemorrhagic stroke; subarachnoid haemorrhage; head injury such as subarachnoid haemorrhage associated with traumatic head injury; ulcers; allergies; benign prostatic hypertrophy; chronic renal failure; renal disease; impaired glucose tolerance; migraine; hyperalgesia; pain; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g. HIV, post-polio syndrome, and post-herpetic neuralgia; phantom limb pain; labour pain; cancer pain; post-chemotherapy pain; post-stroke pain; post-operative pain; neuralgia; conditions associated with visceral pain including irritable bowel syndrome, migraine and angina; urinary bladder incontinence e.g. urge incontinence; tolerance to narcotics or withdrawal from narcotics; sleep disorders; sleep apnea; narcolepsy; insomnia; parasomnia; jet-lag syndrome; and neurodegenerative disorders, which includes nosological entities such as disinhibition-dementia-parkinsonism-amyotrophy complex; pallido-ponto-nigral degeneration, epilepsy, and seizure disorders.

Experiments have shown that central administration of the ligand orexin-A (described in more detail below) stimulated food intake in freely-feeding rats during a 4 hour time period. This increase was approximately four-fold over control rats receiving vehicle. These data suggest that orexin-A may be an endogenous regulator of appetite. Therefore, antagonists of its receptor may be useful in the treatment of obesity and diabetes, see *Cell*, 1998, 92, 573–585.

There is a significant incidence of obesity in westemised societies. According to WHO definitions a mean of 35% of subjects in 39 studies were overweight and a further 22% clinically obese. It has been estimated that 5.7% of all healthcare costs in the USA are a consequence of obesity. About 85% of Type 2 diabetics are obese, and diet and exercise are of value in all diabetics. The incidence of diagnosed diabetes in westernised countries is typically 5% and there are estimated to be an equal number undiagnosed. The incidence of both diseases is rising, demonstrating the inadequacy of current treatments which may be either ineffective or have toxicity risks including cardiovascular effects. Treatment of diabetes with sulfonylureas or insulin can cause hypoglycaemia, whilst metformin causes GI side-effects. No drug treatment for Type 2 diabetes has been shown to reduce the long-tern complications of the disease. Insulin sensitisers will be useful for many diabetics, however they do not have an anti-obesity effect.

Rat sleep/EEG studies have also shown that central administration of orexin-A, an agonist of the orexin receptors, causes a dose-related increase in arousal, largely at the expense of a reduction in paradoxical sleep and slow wave sleep 2, when administered at the onset of the normal sleep period. Therefore antagonists of its receptor may be useful in the treatment of sleep disorders including insomnia.

International Patent Applications PCT/GB98/02437 and PCT/EP99/03100 (published after the priority date of the present application) disclose various phenyl urea derivatives as orexin receptor antagonists.

The present invention provides phenyl urea and phenyl thiourea derivatives which are non-peptide antagonists of human orexin receptors, in particular orexin-1 receptors. In particular, these compounds are of potential use in the treatment of obesity including obesity observed in Type 2 (non-insulin-dependent) diabetes patients and/or sleep disorders.

According to the invention there is provided a compound of formula (I):

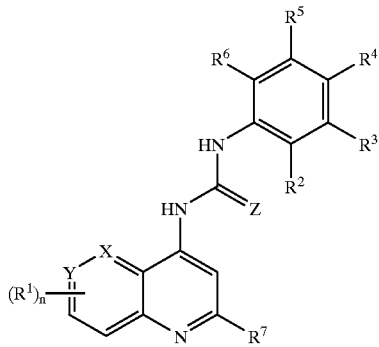

(I)

in which:
one of X and Y is N and the other is CH;
Z represents oxygen or sulfur;
$R^1$ represents $(C_{1-6})$alkyl, $(C_{2-6})$alkenyl or $(C_{1-6})$alkoxy, any of which may be optionally substituted; halogen, $R^8CO—$ or $NR^9R^{10}CO—$;
$R^2$, $R^3$, $R^4$, $R^5$ and $R^6$ independently represent $(C_{1-6})$alkyl, $(C_{2-6})$alkenyl, $(C_{1-6})$alkoxy or $(C_{1-6})$alkylthio, any of which may be optionally substituted; hydrogen, halogen, nitro, cyano, aryloxy, aryl$(C_{1-6})$alkyloxy, aryl $(C_{1-6})$alkyl, $R^8CO—$, $R^8SO_2NH—$, $R^8SO_2O—$, $R^8CON(R^{11})—$, $NR^9R^{10}—$, $NR^9R^{10}CO—$, $—COOR^9$, $R^{11}C(=NOR^8)$, heterocyclyl or heterocyclyl$(C_{1-6})$alkyl;
or an adjacent pair of $R^2$, $R^3$, $R^4$, $R^5$ and $R^6$ together with the carbon atoms to which they are attached form an optionally substituted carbocyclic or heterocyclic ring;
$R^7$ is $(C_{1-6})$alkyl, $(C_{2-6})$alkenyl, $(C_{1-6})$alkoxy or $(C_{1-6})$alkylthio, any of which may be optionally substituted; halogen, hydroxy, nitro, cyano, $NR^9R^{10}—$, $NR^9R^{10}CO—$, $N_3$, $—OCOR^9$ or $R^8CON(R^{11})—$;
$R^8$ is $(C_{1-6})$alkyl, $(C_{2-6})$alkenyl, heterocyclyl, heterocyclyl$(C_{1-6})$alkyl, heterocyclyl$(C_{2-6})$alkenyl, aryl, aryl$(C_{1-6})$alkyl or aryl$(C_{1-6})$alkenyl any of which may be optionally substituted;
$R^9$ and $R^{10}$ independently represent hydrogen, $(C_{1-6})$alkyl, $(C_{2-6})$alkenyl, heterocyclyl, heterocyclyl$(C_{1-6})$alkyl, aryl or aryl$(C_{1-6})$alkyl, any of which may be optionally substituted;
$R^{11}$ is hydrogen or $(C_{1-6})$alkyl; and
n is 0, 1, 2, or 3;
or a pharmaceutically acceptable salt thereof.

In formula (I) Z is preferably oxygen.
When a halogen atom is present in the compound of formula (I) this may be fluorine, chlorine, bromine or iodine.
n is preferably 0 or 1, more preferably 0.
X is preferably N and Y is CH.
The CH group represented by X or Y may be substituted by a group $R^1$.
When n is 1, the group $R^1$ is preferably in the 6- or 8-position, particularly the 8-position.
$R^1$ is preferably halogen e.g. fluoro, or $(C_{1-6})$alkoxy e.g. methoxy. $R^1$ is most preferably fluoro.
When any one of $R^1$ to $R^{11}$ comprise a $(C_{1-6})$alkyl group, whether alone or forming part of a larger group, e.g. alkoxy or alkylthio, the alkyl group may be straight chain, branched or cyclic, or combinations thereof, it preferably contains 1 to 4 carbon atoms, and is most preferably methyl or ethyl.
When any one of $R^1$ to $R^{10}$ comprise a $(C_{2-6})$alkenyl group, whether alone or forming part of a larger group, the alkenyl group may be straight chain, branched or cyclic, or combinations thereof, it preferably contains 2 to 4 carbon atoms and is most preferably alkyl.

Suitable optional substituents for $(C_{1-6})$alkyl, $(C_{2-6})$alkenyl, $(C_{1-6})$alkoxy and $(C_{1-6})$alkylthio groups include one or more substituents selected from halogen e.g. fluoro, $(C_{1-4})$alkoxy e.g. methoxy, hydroxy, carboxy and $(C_{1-6})$alkyl esters and $(C_{1-6})$alkylamides thereof, amino, mono- or di-$(C_{1-6})$alkylamino, $N(R^{11})COR^8$, $N(R^{11})SO_2R^8$, $CONR^9R^{10}$ and cyano. For example one or more substituents selected from halogen e.g. fluoro, $(C_{1-4})$alkoxy e.g. methoxy, hydroxy, carboxy and $(C_{1-6})$alkyl esters thereof, amino, mono- or di-$(C_{1-6})$alkylamino and cyano.

When used herein the term "aryl", whether alone or forming part of a larger group, includes optionally substituted aryl groups such as phenyl and naphthyl, preferably phenyl. The aryl group may contain up to 5, more preferably 1, 2 or 3 optional substituents. Suitable substituents for aryl groups include halogen, $(C_{1-4})$alkyl e.g. methyl, $(C_{1-4})$ haloalkyl e.g. trifluoromethyl, $(C_{1-4})$alkoxy e.g. methoxy, $(C_{1-4})$alkoxy$(C_{1-4})$alkyl e.g. methoxymethyl, hydroxy, =O, carboxy and $(C_{1-6})$alkyl esters and $(C_{1-6})$mono and dialkylamides thereof, nitro, arylsulfonyl e.g. p-toluenesulfonyl, $(C_{1-4})$alkylsulfonyl e.g. methanesulfonyl, aryl$(C_{1-4})$alkyl e.g. benzyl or 3-phenylpropyl, aryl e.g. phenyl, hydroxy $(C_{1-4})$alkyl e.g. hydroxyethyl, $R^3CO_2—$, $R^aCO_2(C_{1-4})$alkyl e.g. carboethoxypropyl, cyano, cyano$(C_{1-4})$alkyl e.g. 3-cyanopropyl, $R^3R^bN$, $R^aR^bN(C_{1-4})$alkyl, $R^aR^bNCO(C_{1-4})$ alkyl in which $R^a$ and $R^b$ are independently selected from hydrogen and $(C_{1-4})$alkyl.

When any one of $R^2$ to $R^6$, $R^8$, $R^9$ or $R^{10}$ represent heterocyclyl or heterocyclyl$(C_{1-6})$alkyl the heterocyclyl group is preferably a 5- to 10-membered monocyclic or bicyclic ring, which may be saturated or unsaturated, for example containing 1, 2 or 3 heteroatoms selected from oxygen, nitrogen and sulfur; for example pyrrolidine, oxazole, morpholine, pyrimidine or phthalimide. A ring containing one or two nitrogen atoms is especially preferred. The heterocyclyl group may contain up to 5, more preferably 1, 2 or 3 optional substituents. Suitable substituents for heterocyclyl groups include those mentioned above for aryl groups.

When an adjacent pair of $R^2$ to $R^6$ together with the carbon atoms to which they are attached form a carbocyclic or heterocyclic ring this is preferably a 5- to 7-membered ring, which may be aromatic or non-aromatic. Heterocyclic rings preferably contain 1, 2 or 3 heteroatoms selected from oxygen, nitrogen and sulfur, for example oxazole, imidazole, thiophene, pyran, dioxan, pyrrole or pyrrolidine. A ring containing one nitrogen atom and one oxygen atom is preferred. It is particularly preferred for the nitrogen to be attached directly to the $R^4$ position. A carbocyclic or heterocyclic ring formed by an adjacent pair of $R^2$ to $R^6$ together with the carbon atoms to which they are attached may be optionally substituted on carbon or nitrogen by one or more substituents, e.g. up to 3 substituents. Suitable substituents for the carbocyclic or heterocyclic ring include those mentioned above for aryl groups.

Preferably at least one of $R^2$ to $R^6$ is other than hydrogen.

A preferred group of compounds are those in which $R^2$ to $R^6$ independently represent hydrogen, $R^8CO—$, $NR^9R^{10}CO—$, halogen, $(C_{1-6})$alkoxy e.g. methoxy. $(C_{1-6})$alkylthio e.g. methylthio, or $NR^9R^{10}$ wherein $R^9$ and $R^{10}$ preferably represent $(C_{1-6})$alkyl e.g. dimethylamino, and at least one of $R^2$ to $R^6$ is other than hydrogen: or an adjacent pair of $R^2$ to $R^6$ together with the carbon atoms to which they are attached form an optionally substituted 5- to 7-membered carbocyclic or heterocyclic ring, e.g. a 6- or 7-membered non-aromatic heterocyclic ring, a 5- or 6membered non-aromatic carbocyclic ring or a 5- or 6-membered aromatic heterocyclic ring.

A further preferred group of compounds are those in which $R^2$, $R^5$ and $R^6$ represent hydrogen.

A further preferred group of compounds are those in which $R^2$, $R^4$ and $R^6$ represent hydrogen.

A further preferred group of compounds are those in which either $R^3$ and $R^4$, or $R^3$ and $R^5$ are other than hydrogen.

A group of compounds which may be mentioned are the compounds of formula (Ia):

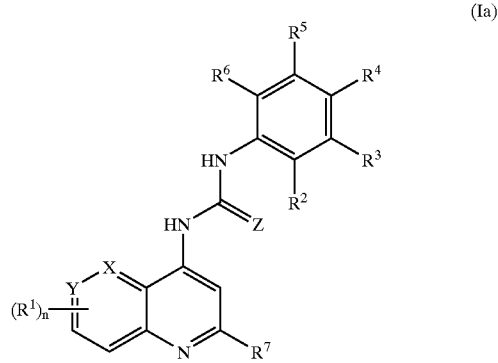

(Ia)

in which:
one of X and Y is N and the other is CH;
Z represents oxygen or sulfur;
$R^1$ represents $(C_{1-6})$alkyl, $(C_{2-6})$alkenyl or $(C_{1-6})$alkoxy, any of which may be optionally substituted; halogen, $R^8CO$— or $NR^9R^{10}CO$—;
$R^2$, $R^3$, $R^4$, $R^5$ and $R^6$ independently represent $(C_{1-6})$alkyl, $(C_{2-6})$alkenyl, $(C_{1-6})$alkoxy or $(C_{1-6})$alkylthio, any of which may be optionally substituted; hydrogen, halogen, nitro, cyano, aryloxy, aryl$(C_{1-6})$alkyloxy, aryl $(C_{1-6})$alkyl, $R^8CO$—, $R^8SO_2NH$—, $R^8CON(R^{11})$—, $NR^9R^{10}$—, $NR^9R^{10}CO$—, —$COOR^9$, heterocyclyl or heterocyclyl$(C_{1-6})$alkyl;
or an adjacent pair of $R^2$, $R^3$, $R^4$, $R^5$ and $R^6$ together with the carbon atoms to which they are attached form an optionally substituted carbocyclic or heterocyclic ring;
$R^7$ is $(C_{1-6})$alkyl, $(C_{2\ 6})$alkenyl, $(C_{1-6})$alkoxy or $(C_{1-6})$ alkylthio, any of which may be optionally substituted; halogen, hydroxy, nitro, cyano, $NR^9R^{10}$—, $NR^9R^{10}CO$—, $N_3$, —$OCOR^9$ or $R^8CON(R^{11})$—;
$R^8$ is $(C_{1-6})$alkyl, or aryl;
$R^9$ and $R^{10}$ independently represent hydrogen, $C_{1-6}$ alkyl, aryl or aryl $(C_{1-6})$alkyl;
$R^{11}$ is hydrogen or $(C_{1-6})$alkyl; and
n is 0, 1, 2, or 3;
or a pharmaceutically acceptable salt thereof.

In the compounds of formula (Ia) suitable substituents for aryl groups and for heterocyclyl groups when any one of $R^2$ to $R^6$ represent heterocyclyl or heterocyclyl$(C_{1-6})$alkyl include halogen, $(C_{1-4})$alkyl e.g. methyl, $(C_{1-4})$haloalkyl e.g. trifluoromethyl, $(C_{1-4})$alkoxy e.g. methoxy, $(C_{1-4})$alkoxy $(C_{1-4})$alkyl e.g. methoxymethyl, hydroxy, carboxy and $(C_{1-6})$alkyl esters, amino, nitro, arylsulfonyl e.g. p-toluenesulfonyl, and $(C_{1-4})$alkylsulfonyl e.g. methanesulfonyl. Suitable substituents for carbocyclic or heterocyclic rings when an adjacent pair of $R^2$ to $R^6$ together with the carbon atoms to which they are attached form a carbocyclic or heterocyclic ring include $(C_{1-4})$alkyl e.g. methyl, $(C_{1-4})$ alkoxy, $(C_{1-4})$alkoxy$(C_{1-4})$alkyl e.g. methoxymethyl, hydroxy, =O, aryl$(C_{1-4})$alkyl e.g. benzyl or 3-phenylpropyl, aryl e.g. phenyl, hydroxy$(C_{1-4})$alkyl e.g. hydroxyethyl, $R^aCO_2$—, $R^aCO_2$ $(C_{1-4})$alkyl e.g. carboethoxypropyl, cyano, cyano$(C_{1-4})$alkyl e.g. 3-cyanopropyl, $R^aR^bN$ and $R^aR^bN(C_{1-4})$alkyl in which $R^a$ and $R^b$ are independently selected from hydrogen and $(C_{1-4})$alkyl.

A further group of compounds of formula (Ia) are those in which $R^2$ to $R^6$ independently represent hydrogen, halogen, $(C_{1-6})$alkoxy e.g. in ethoxy, $(C_{1-6})$alkylthio e.g. methylthio, or $NR^9R^{10}$ wherein $R^9$ and $R^{10}$ preferably represent $(C_{1-6})$ alkyl e.g. dimethylamino, and at least one of $R^2$ to $R^6$ is other than hydrogen; or an adjacent pair of $R^2$ to $R^6$ together with the carbon atoms to which they are attached form an optionally substituted 5- to 7-membered heterocyclic ring, e.g. a 6- or 7-membered non-aromatic heterocyclic ring or a 5- or 6-membered aromatic heterocyclic ring.

Particular compounds according to the invention include those mentioned in the examples and their pharmaceutically acceptable salts.

It will be appreciated that for use in medicine the salts of the compounds of formula (I) should be pharmaceutically acceptable. Suitable pharmaceutically acceptable salts will be apparent to those skilled in the art and include for example acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention. Also included within the scope of the invention are solvates and hydrates of compounds of formula (I).

The invention extends to all isomeric forms including stereoisomers and geometric isomers of the compounds of formula (I) including enantiomers and mixtures thereof e.g. racemates. The different isomeric forms may be separated or resolved one from the other by conventional methods, or any given isomer may be obtained by conventional synthetic methods or by stereospecific or asymmetric syntheses.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

According to a further aspect the invention provides a process for the preparation of the compounds of formula (I) and salts thereof which comprises coupling a compound of formula (II);

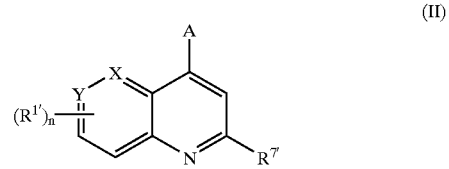

(II)

with a compound of formula (III);

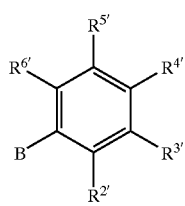

(III)

wherein A and B are appropriate functional groups to form the —NHCONH— or —NHCSNH— moiety when coupled; n, X and Y are as defined in formula (I); and $R^1$ to $R^7$ are $R^1$ to $R^7$ as defined in formula (I) or groups convertible thereto; and thereafter optionally and as necessary and in any appropriate order, converting any $R^1$ to $R^7$ when other than $R^1$ to $R^7$ respectively to $R^1$ to $R^7$, and/or forming a pharmaceutically acceptable salt thereof.

Suitable examples of groups A and B are:
(i) A and B are —$NH_2$
(ii) one of A and B is —$CON_3$ and the other is —$NH_2$
(iii) one of A and B is —$CO_2H$ and the other is —$NH_2$
(iv) one of A and B is —N=C=O and the other is —$NH_2$
(v) one of A and B is —N=C=S and the other is —$NH_2$
(vi) one of A and B is —NHCOL and the other is —$NH_2$
(vii) one of A and B is halogen and the other is —$NHCONH_2$
(viii) one of A and B is —$NHCOCBr_3$ and the other is $NH_2$ Wherein L is a leaving group, such as chloro or bromo, imidazole or phenoxy or phenylthio optionally substituted for example with halogen, for example chlorine.

When A and B are both —$NH_2$, the reaction is generally effected in the presence of a urea coupling agent such as 1,1'-carbonyldiimidazole or triphosgene.

When one of A and B is —$CO_2H$ and the other is —$NH_2$ the reaction is generally effected in the presence of an agent such as diphenylphosphoryl azide and in the presence of a base such as triethylamine.

When one of A and B is —N=C=O or —N=C=S and the other is —$NH_2$ the reaction is suitably carried out in an inert solvent for example dimethylformamide (DMF) or dichloromethane (DCM) and/or toluene at ambient or elevated temperature, preferably ambient.

When one of A and B is —$CON_3$ or —$CO_2H$ and the other is —$NH_2$ the reaction is suitably carried out in an inert solvent for example toluene or DMF at elevated temperature.

Where one of A and B is —NHCOL and the other is —$NH_2$, the reaction is suitably carried out in an inert solvent such as DCM at ambient temperature optionally in the presence of a base, such as triethylamine or in DMF at ambient or elevated temperature.

When one of A and B is halogen and the other is —$NHCONH_2$ the reaction is suitably carried out in an inert solvent such as toluene at elevated temperature, optionally in the presence of base.

When one of A and B is —$NHCOCBr_3$ and the other is $NH_2$ the reaction is suitably carried out in an inert solvent such as dimethylsulfoxide or pyridine at elevated temperatures in the presence of a base such as DBU.

Suitable examples of compounds having groups $R^1$ to $R^7$ which are convertible to $R^1$ to $R^7$ respectively include compounds where one or more of $R^2$ to $R^7$ are OH or $NH_2$;

and compounds where an adjacent pair of $R^2$ to $R^6$ together with the carbon atoms to which they are attached represent a fused pyrrole ring which is unsubstituted on nitrogen, wherein treatment with a base, e.g. sodium hydride, and reaction with an electrophile, e.g. methyl iodide, benzyl chloride or benzenesulfonyl chloride, affords the corresponding substituent on the pyrrole nitrogen.

Compounds of formula (II) and (III) where A or B is —$NH_2$, $CO_2H$, —N=C=S or halogen are known compounds or can be prepared analogously to known compounds.

Compounds of formula (II) and (III) where A or B is —N=C=O may be prepared by treating a compound of formula (II) or (III) in which:
(i) A or B is —$NH_2$, with phosgene or a phosgene equivalent, in the presence of excess base or an inert solvent.
(ii) A or B is —$CON_3$, via the nitrene, by thermal rearrangement using conventional conditions (*Helv. Chim. Acta*, 1987, 70, 262).
(iii) A or B is —$CONH_2$. via the nitrene intermediate using conventional conditions.

Compounds of formula (II) and (III) where A or B is —NHCOL may be prepared by reacting a compound of formula (II) or (III) in which A or B is —$NH_2$ with phosgene or a phosgene equivalent, in an inert solvent, at low temperature, if necessary in the presence of a base such as triethylamine. Examples of phosgene equivalents include triphosgene, 1,1'-carbonyldiimidazole, phenyl chloroformate and phenyl chlorothioformate.

Compounds of formula (II) and (III) where A or B is —$NHCONH_2$ can be prepared from compounds of formula (II) or (III) where A or B is —$NH_2$ by reaction with an inorganic isocyanate under conventional conditions.

Compounds of formula (II) and (III) where A or B is —$NHCOCBr_3$ can be prepared from compounds of formula (II) or (III) where A or B is —$NH_2$ by reaction with tribromoacetyl chloride in an inert solvent such as DCM in the presence of a base such as triethylamine.

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial 'split and mix' approach or by multiple parallel synthesis using either solution phase or solid phase chemistry, by procedures known to those skilled in the art.

According to a further aspect the invention provides a compound library comprising at least 2 compounds of formula (I), or pharmaceutically acceptable salts thereof.

Novel intermediates of formulae (II) and (III) are also part of this invention.

According to a further aspect the invention provides a compound of formula (II):

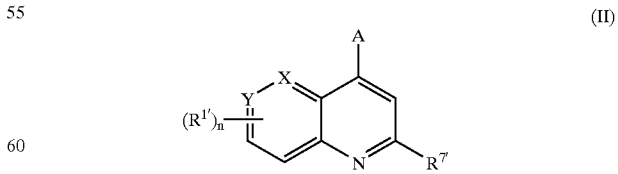

(II)

wherein A is —NH, —$CON_3$, —$CO_2H$, —N=C=O, —N=C=S, —NHCOL, halogen or —$NHCOCBr_3$ and L is a leaving group, n, X and Y are as defined in formula (I), and $R^{1'}$ and $R^{7'}$ are $R^1$ and $R^7$ as defined in formula (I) or groups convertible thereto.

Pharmaceutically acceptable salts may be prepared conventionally by reaction with the appropriate acid or acid derivative.

As indicated above the compounds of formula (I) and their pharmaceutically acceptable salts are useful for the treatment of diseases or disorders where an antagonist of a human orexin receptor is required especially feeding disorders, such as obesity and diabetes; prolactinoma; hypoprolactinemia, hypothalamic disorders of growth hormone deficiency; idiopathic growth hormone deficiency; Cushings syndrome/disease; hypothalamic-adrenal dysfunction; dwarfism; sleep disorders; sleep apnea; narcolepsy; insomnia; parasomnia; jet-lag syndrome; and sleep disturbances associated with such diseases as neurological disorders, neuropathic pain, restless leg syndrome, heart and lung diseases; depression; anxiety; addictions; obsessive compulsive disorder; affective neurosis/disorder; depressive neurosis/disorder; anxiety neurosis; dysthymic disorder; behaviour disorder; mood disorder; sexual dysfunction; psychosexual dysfunction; sex disorder; sexual disorder; schizophrenia; manic depression; delirium; dementia; bulimia; and hypopituitarism.

The compounds of formula (I) and their pharmaceutically acceptable salts are particularly useful for the treatment of obesity, including obesity associated with Type 2 diabetes, and sleep disorders.

Other diseases or disorders which may be treated in accordance with the invention include disturbed biological and circadian rhythms; adrenohypophysis disease; hypophysis disease; hypophysis tumor/adenoma; adrenohypophysis hypofunction; functional or psychogenic amenorrhea; adrenohypophysis hyperfunction; migraine; hyperalgesia; pain; enhanced or exaggerated sensitivity to pain such as hyperalgesia, causalgia and allodynia; acute pain; bum pain; atypical facial pain; neuropathic pain; back pain; complex regional pain syndromes I and II; arthritic pain; sports injury pain; pain related to infection, e.g. HIV, post-polio syndrome and post-herpetic neuralgia; phantom limb pain; labour pain; cancer pain; post-chemotherapy pain; post-stroke pain; post-operative pain; neuralgia; and tolerance to narcotics or withdrawal from narcotics.

According to a further aspect the invention provides a method of treating or preventing diseases or disorders where an antagonist of a human orexin receptor is required, which comprises administering to a subject in need thereof an effective amount of a compound of formula (I), or a pharmaceutically acceptable salt thereof.

According to a further aspect the invention provides a compound of formula (I), or a pharmaceutically acceptable salt thereof, for use in the treatment or prophylaxis of diseases or disorders where an antagonist of a human orexin receptor is required.

According to a further aspect the invention provides the use of a compound of formula (I), or a pharmaceutically acceptable salt thereof, in the manufacture of a medicament for the treatment or prophylaxis of diseases or disorders where an antagonist of a human orexin receptor is required.

For use in medicine, the compounds of the present invention are usually administered as a pharmaceutical composition. The present invention also provides a pharmaceutical composition comprising a compound of formula (I), or a pharmaceutically acceptable salt thereof, and a pharmaceutically acceptable carrier.

The compounds of formula (I) and their pharmaceutically acceptable salts may be administered by any convenient method, for example by oral, parenteral, buccal, sublingual, nasal, rectal or transdermal administration and the pharmaceutical compositions adapted accordingly.

The compounds of formula (I) and their pharmaceutically acceptable salts which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon or hydrofluorocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

The dose of the compound of formula (I), or a pharmaceutically acceptable salt thereof, used in the treatment or prophylaxis of the abovementioned disorders or diseases will vary in the usual way with the particular disorder or disease being treated, the weight of the subject and other similar factors. However as a general rule suitable unit doses may be 0.05 to 1000 mg, more suitably 0.05 to 500 mg; such unit doses may be administered more than once a day for example two or three times a day, so that the total daily dosage is in the range of about 0.01 to 100 mg/kg; and such therapy may extend for a number of weeks or months. In the case of physiologically acceptable salts the above figures are calculated as the parent compound of formula (I).

No toxicological effects are indicated/expected when a compound of formula (I) is administered in the above mentioned dosage range.

Human orexin-A, referred to above, has the amino acid sequence:

pyroGlu Pro Leu Pro Asp Cys Cys Arg Gln Lys Thr
1               5                       10

Cys Ser Cys Arg Leu Tyr Glu Leu Leu His Gly Ala
       15                          20

Gly Asn His Ala Ala Gly Ile Leu Thr Leu-NH$_2$
       25                   30

Orexin-A can be employed in a process for screening for compounds (antagonists) which inhibit the ligand's activation of the orexin-1 receptor.

In general, such screening procedures involve providing appropriate cells which express the orexin-1 receptor on the surface thereof. Such cells include cells from mammals, yeast, Drosophila or *E coli*. In particular, a polynucleotide encoding the orexin-1 receptor is employed to transfect cells to thereby express the receptor. The expressed receptor is then contacted with a test compound and an orexin-1 receptor ligand to observe inhibition of a functional response.

One such screening procedure involves the use of melanophores which are transfected to express the orexin-1 receptor. Such a screening technique is described in WO 92/01810.

Another such screening technique involves introducing RNA encoding the orexin-1 receptor into Xenopus oocytes to transiently express the receptor. The receptor oocytes may then be contacted with a receptor ligand and a compound to be screened, followed by detection of inhibition of a signal in the case of screening for compounds which are thought to inhibit activation of the receptor by the ligand.

Another method involves screening for compounds which inhibit activation of the receptor by determining inhibition of binding of a labelled orexin-1 receptor ligand to cells which have the receptor on the surface thereof. Such a method involves transfecting a eukaryotic cell with DNA encoding the orexin-1 receptor such that the cell expresses the receptor on its surface and contacting the cell or cell membrane preparation with a compound in the presence of a labelled form of an orexin-1 receptor ligand. The ligand can be labelled, e.g. by radioactivity. The amount of labelled ligand bound to the receptors is measured, e.g. by measuring radioactivity of the receptors. If the compound binds to the receptor as determined by a reduction of labelled ligand which binds to the receptors, the binding of labelled ligand to the receptor is inhibited.

Yet another screening technique involves the use of FLIPR equipment for high throughput screening of test compounds that inhibit mobilisation of intracellular calcium ions, or other ions, by affecting the interaction of an orexin-1 receptor ligand with the orexin-1 receptor. The ligand used in the screening method described below to determine the antagonist activity of compounds according to the invention is orexin-A which has the amino acid sequence shown above.

All publications, including but not limited to patents and patent applications, cited in this specification are herein incorporated by reference as if each individual publication were specifically and individually indicated to be incorporated by reference herein as though fully set forth.

The following Examples illustrate the preparation of compounds of the invention. In the Examples $^1$H NMR's were measured at 250 MHz in d$_6$-DMSO unless otherwise stated. All hydrochloride salts unless otherwise stated were prepared by dissolving/suspending the free-base in methanol and treating with an excess of ethereal HCl (1M).

DESCRIPTION 1

Trifluoromethane Sulfonic Acid 2-Methyl-[1,5] naphthyridin-4-yl Ester (D1)

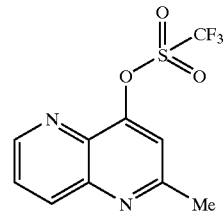

A suspension of 4-hydroxy-2-methyl-[1,51]-naphthyridine contaminated with 4-hydroxy-2-methyl-[1, 7]-naphthyridine (1.0g) (*J. Royal Netherlands Chem. Soc.* 1976, 95, 220) in DCM (45 ml) was treated sequentially with 2.6-lutidine (1.2 ml), 4-N,N-dimethylaminopyridine (0.075 g) and trifluoromethanesulfonic anhydride (1.2 ml). After the final addition was complete tile mixture was stirred for 30 min, washed with saturated aqueous ammonium chloride. dried (Na$_2$SO$_4$) and solvent removed at reduced pressure. The residue was column chromatographed (silica gel, 0–20% ethyl acetate in peitanie) to give after combining the appropriate fractions the title compound (0.588 g) as a colourless solid. $^1$H NMR (CDCl$_3$) δ: 2.84 (3H, s), 7.42 (1H, s), 7.73 (1H, dd), 8.37 (1H, dd), 9.04 (1H, m).

DESCRIPTION 2

4-Amino-2-methyl-[1,5]-naphthyridine (D2)

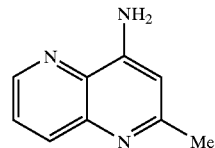

D1 (2.2 g) and n-propylamine hydrochloride (2.34 g) were combined in pyridine (75 ml) and the mixture refluxed for 8 h. Solvent was removed at reduced pressure, the residue dissolved in 2N sodium hydroxide and extracted with diethyl ether (×3) and DCM (×2). The combined organic phase was dried (Na$_2$SO$_4$) and solvent removed at reduced pressure. The residue was triturated with pentane to give the title compound (1.32 g) as a pale orange solid. $^1$H NMR (CDCl$_3$) δ: 2.60 (3H, s), 5.44 (2H, bs), 6.66 (1H, s), 7.54 (1H, dd), 8.17 (1H, dd), 8.67 (1H, m).

DESCRIPTION 3

3-Chloro-4-methanesulfonyloxybenzoic Acid (D3)

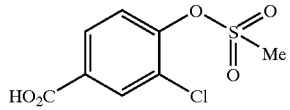

Sodium hydroxide (1.67 g) and 3-chloro4-hydroxybenzoic acid (3.0 g) were combined in water (30 ml) and stirred until dissolution was complete. Methanesulfonic anhydride (3.33 g) in DCM (15 ml) was added with cooling (ice bath) and the mixture stirred for 48 h. The organic phase was separated and the aqueous phase acidified with conc. HCl. The precipitated colourless solid was separated by filtration, washed with water and recrystallised from methanol to give the title compound (1.85 g) as a colourless solid. m/z (API+): 249, 251 (MH+).

DESCRIPTION 4

2-Methoxy-5-[3-(2-methyl-[1,5]-naphthyridin-4-yl)ureido]benzoic Acid

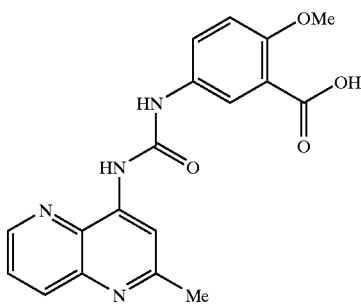

The compound of Example 1 (0.155 g) was added to sodium hydroxide (0.09 g) in 10% aqueous methanol and warmed to 80° C. for 6 h. Solvent was removed at reduced pressure the gum dissolved in water (3 ml) and acidified with 2N HCl to give the title compound (0.09 g) after filtration and washing with water and diethyl ether. $^1$H NMR δ: 2.88 (3H, s), 3.8] (3H, s), 7.15 (1H, d), 7.60 (1H, dd), 7.95 (1H, d), 8.11 (1H, m), 8.62 (2H, m), 9.14 (1H, m), 10.53 (1H, s), 10.68 (1H, s).

DESCRIPTION 5

7-Amino-2-cyclopropylimethyl-4-methyl-2H-isoquinolin-1-one (D5)

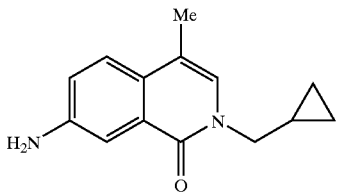

Step 1: 4-Methyl-7-nitro-3,4-dihydro-2H-isoquinolin-1-one
A solution of 4-methyl-3,4-dihydro-2H-isoquinolin-1-one (1. 0g) (*J. Med. Chem.*, 1988, 31, 433) in conc. sulfuric acid (5 ml) was added dropwise over 20 min to an ice cooled solution of potassium nitrate (0.678 g) in conc. sulfuric acid (5 ml). The mixture was stirred for a further 30 min with ice-cooling. The mixture was added dropwise to ice (150 g) with stirring. The precipitated solid was collected by filtration, washed with water and dried to give the sub-titl compound (0.95 g). $^1$H NMR δ: 1.28 (3H, d, J=6.6 Hz), 3.14–3.28 (1H, m), 3.52 (2H, m), 7.67 (1H, d, J=8.5 Hz), 8.29 (1H, s), 8.35 (1H, dd, J=2.5, 8.4 Hz) (1H, d, J=2.5 Hz).

Step 2: 2-Cyclopropylmethyl-4-methyl-7-nitro-2H-isoquinolin-1-one

To 4-methyl-7-nitro-3,4-dihydro-2H-isoquinolin-1-one (0.90 g) in DMF (30 ml), sodium hydride (0.212 g, 60% suspension in oil) was added in portions. The mixture was stirred for 1 h then treated with cyclopropylmethyl bromide (0.72 g). The mixture was stirred for 4 h, poured into water and extracted with ethyl acetate. The organic phase was washed with water, dried (Na$_2$SO$_4$) and solvent removed at reduced pressure. The residue was column chromatographed (silica gel, DCM) to give the sub-title compound (0.22 g) as a yellow solid. $^1$H NMR δ: 0.43–0.54 (4H, m), 1.26 (1H, m), 2.30 (3H, s), 3.84 (2H, d, J 7.2 Hz), 7.70 (1H, s), 7.91 (1H, d, J=9.0 Hz), 8.50 (1H, dd, J=2.5, 8.9 Hz), 8.98 (1H, d, J=2.5 Hz).

Step 3: 5-Amino-2-cyclopropylmethyl-4-methyl-2H-isoquinolin-1-one

2-Cyclopropylmethyl-4-methyl-7-nitro-2H-isoquinolin-1-one (0.20 g) in ethanol (20 ml) containing 10% Pd/C was stirred under hydrogen (1 atm.) for 4 h. The mixture was filtered (kieselguhr) and solvent removed to give the title compound (0.195 g). $^1$H NMR δ: 0.33–0.48 (4H, m), 1.19 (1H, m), 2.15 (3H, s), 3.73 (2H, d, J=7.2 Hz), 5.22 (2H, s), 7.02 (1H, dd, J=2.5, 8.7 Hz), 7.39 (2H, m).

DESCRIPTION 6

5-Amino-N-cyclopropylmethyl-2-methoxy-benzamide (D6)

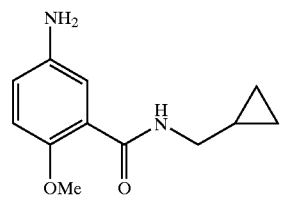

Step 1: N-cyclopropylmethyl-2-methoxy-5-nitrobenzamide—A solution of 2-methoxy-5-nitrobenzoic acid (4.9 g) (*Rec. Trav. Chim. Pays-Bas*, 1936, 737) and cyclopropylmethyl amine (1.75 g) in dimethylformamide was treated with N-hydroxybenzotriazole (0.2 g) and EDC.HCl (4.74 g). The mixture was stirred for 24 h. Saturated sodium hydrogen carbonate was added, the mixture stirred for 3 h and the precipitate collected as the title compound (6.95 ). m/z (API+): 251 (MH+).

Step 2: 5-Amino-N-cyclopropylmethyl-2-methoxy-benzamide—(2.57 g) was prepared from N-cyclopropylmethyl-2-methoxy-5-nitrobenzamide (3.6 g) according to the method of D21 step 2. m/z (API+): 231 (MH+). $^1$H NMR (CDCl$_3$) δ: 0.26 (2H, m), 0.51–0.55 (2H, m), 3.33 (1H, m), 3.55 (2H, brs), 3.90 (3H, s), 6.79 (2H, m), 7.56 (1H, dd, J=0.5, 2.8 Hz), 8.08 (1H, brs).

This compound was used for the preparation of Example 2.

15

DESCRIPTION 7

3-((E)-3-Furan-2-yl-allanoyl)-4-methoxy-benzoic Acid (D7)

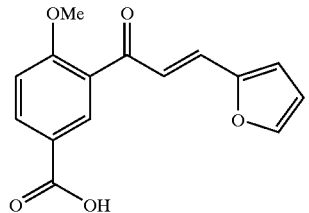

Step 1: 3-(2-Bromo-ethanoyl)-4-methoxy-benzoic acid ethyl ester—3-Acltyl-4-methoxy benzoic acid ethyl ester (5.0 g) in dichloromethane (100 ml) was treated with bromine (1.1 ml) in dichloromethane (100 ml) dropwisde over 3 h with ice coiling. The reaction mixture was then stirred at room temperature for 16 h, solvent removed at reduced pressure and the residue chromatographed (silica gel, dichloromethane eluant to give the title compound (4.4 g). $^1$H NMR (CDCl$_3$) δ: 1.40 (3H, t, J=7.2 Hz), 4.02 (3H, s), 4.37 (2H, q, J=7.2 Hz), 4.56 (2H, s), 7.04 (1H, d, J=8.8 Hz), 8.21 (1H, dd, J 2.4, 8.8 Hz), 8.47 (1H, d, J=2.4 Hz).

Step 2: (5-Ethoxycarbonyl-2-methoxy-benzyl)-triphenyl-phosphonium bromide—-3-(2-Bromo-lthanoyl)-4-methoxy-benzoic acid ethyl ester (0.60 g) was in acetonitrile (10 ml) was treated with triphenylphosphine (0.52 g) for 4 h. Solvent was then removed at reduced pressure and column chromatographed (silica gel, dichloromethane then 5% methanol dichloromethane) to give the title compound (0.63 g). $^1$H NMR (CDCl$_3$) δ: 1.35 (3H, t, J=7.2 Hz), 4.21 (3H, s), 4.31 (2H, q, J=7.2 Hz), 6.28 (2H, d, J=10.8 Hz), 7.07 (1H, d, J=8.8 Hz), 7.63–7.80 (9H, m), 7.89–7.99 (6H, m), 8.20 (1H, dd), 8.28 (1H, s).

Step 3: ((E)-3-Furan-2-yl-allanoyl)-4-methoxy-benzoic acid ethyl ester—A mixture of the phosphonium salt of step 2 (1.0 g), furfuraldehyde (1 ml) and potassium carbonate (0.35 g) in dichloromethane/water (10 ml, 1:1) containing tetrabutyl ammonium hydrogen sulphate (0.05 g) was stirred at 60° C. for 4 h. The reaction mixture was diluted with dichloromethane (30 ml) and water (20 ml), the organic phase separated, solvent removed at reduced pressure and the residue column chromatographed (silica gel, dichloromethane eluant) to give the title compound (0.40 g). $^1$H NMR (CDCl$_3$) δ: 1.39 (3H, t, J=6.8 Hz), 3.96 (3H, s), 4.36 (2H, q, J=6.8 Hz), 6.50 (1H, m), 6.69 (1H, d, J=3.6 Hz), 7.02 (1H, d, J=8.8 Hz), 7.20 (1H, d, J=15.6 Hz), 7.39 (1H, d, J=15.6 Hz), 7.51 (1H, d, J=1.6 Hz), 8.16 (1H, dd, J=8.8, 2 Hz), 8.27 (1H, d, J=2.4 Hz).

Step 4: ((E)-3-Furan-2-yl-allanoyl)-4-methoxy-benzoic acid—((E)-3-Furan-2-yl-allanoyl)-4-methoxy-benzoic acid ethyl ester (0.047 g) in methanol (5 ml) containing 2N sodium hydroxide (1 ml) was heated at 50° C. for 15 min. Solvent volume was reduced to 1 ml and acidified with 2N hydrochloric acid. After diluting with water (10 ml) the preciptated product (20 mg) was collected by filtration. $^1$H NMR (CDCl$_3$) δ: 6.51 (1H, d), 6.69 (1H, m), 7.06 (1H, d, J=8.8 Hz), 7.19 (1H, d, J=15.6 Hz), 7.40 (1H, d, J=15.6 Hz), 7.52 (1H, s), 8.21 (1H, d, J=8.4 Hz), 8.34 (1H, s).

This compound was used to prepare Example 31.

16

EXAMPLE 1

2-Methoxy-5-[3-(2-methyl-[1,5]-naphthyridin-4-yl)ureido]benzoic Acid Methyl Ester

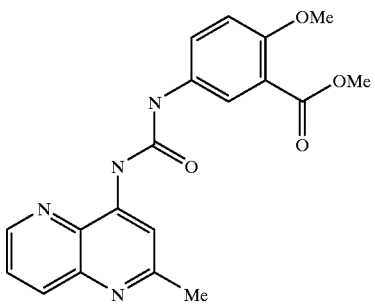

D2 (0.51 g) was added in portions over 10 min to a solution of 1,1'-carbonyl diimidazole (0.536 g) and 4-N,N-dimethylaminopyridine (0.004 g) in DMF (10 ml). The resulting solution was stirred for 16 h, 5-amino-2-methoxybenzoic acid methyl ester (0.577 g) added in DMF (2 ml) and the mixture heated at 100° C. for 2 h. The mixture was diluted with ethyl acetate and washed with water (×2) and brine, dried (Na$_2$SO$_4$) and solvent removed at reduced pressure. The pale pink solid was triturated with DCM to give the title compound (0.58 g). $^1$H NMR δ: 2.64 (3H, s), 3.34 (3H, s), 3.81 (3H, s), 7.15 (1H, d), 7.59 (1H, dd), 7.80 (1H, dd), 7.94 (1H, d), 8.29 (1H, dd), 8.34 (1H, s), 8.89 (1H, m), 9.85 (1H, s), 10.05 (1H, s).

EXAMPLE 2

N-Cyclopropylmethyl-2-methoxy-5-[3-(2-methyl-[1,5]-naphthyridin-4-yl)ureido]benzamide Hydrochloride

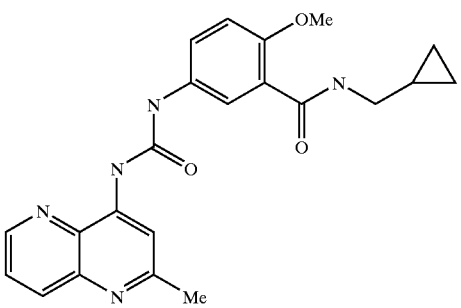

From D2 (0.16 g) and D6 (0.22 g) the title compound was prepared according to the method of Example 1. However the work-up was modified. The reaction mixture was added dropwise to water, chilled and the precipitated solid collected by filtration. The solid was triturated with methanol suspended in methanol and treated with 1M ethereal HCl to give the title compound (0.08 g). $^1$H NMR δ: 0.25 (2H, m), 0.43 (2H, m), 1.23 (1H, m), 2.89 (3H, s), 3.19 (2H, t), 3.90 (3H, s), 7.16 (1H, s), 7.65 (1H, dd), 7.96 (1H, d), 8.12 (1H, dd), 8.30 (1H, t), 8.64 (2H, m), 9.15 (1H, d), 10.54 (1H, s), 10.69 (1H, s).

EXAMPLE 3

1-(2-Methyl-[1,5]-naphthyridin-4-yl)-3-(5-oxo-5,6,7,8-tetrahydronaphthalen-2-yl)urea

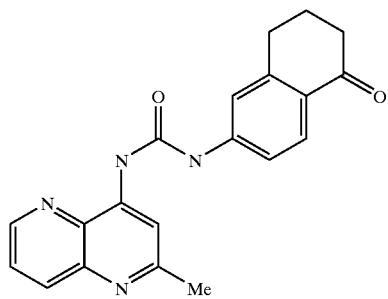

D2 (0.20 g) was added in portions over 3 h to a solution of 1,1'-carbonyl diimidazole (0.203 g) in DCM. When addition was complete the mixture was stirred for a further 2 h. solvent removed at reduced pressure, the residue dissolved in DMF (5 ml) and 6-amino-1,2,3,4-tetrahydronaphthalene-1-one (0.202 g) added. The mixture was heated at 95° C. for 5 h, cooled and solvent removed at reduced temperature. The residue was triturated with water and the resultant solid chromatographed (silica gel, 20% ethyl acetate/pentane and 20–50% ethyl acetate in diethyl ether eluant) to give the title compound (0.134 g) as an orange/yellow solid. $^1$H NMR δ: 2.04 (2H, m), 2.56 (2H, m), 2.65 (3H, s), 2.94 (2H, t), 7.41 (1H, dd), 7.60 (1H, m), 7.79–7.86 (2H, m), 8.30 (1H, dd), 8.36 (1H, s), 8.90 (1H, m), 10.03 (1H, s), 10.36 (1H, s). m/z (API$^+$): 347 (MH$^+$).

EXAMPLE 4

1-(5-Hydroxy-5,6,7,8-tetrahydronaphthalen-2-yl)-3-(2-Methyl-[1,5]-naphthyridin-4-yl)urea

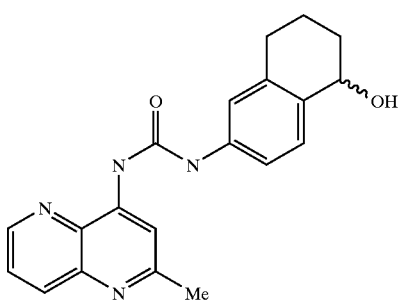

The compound of EXAMPLE 3 (0.093 g) in methanol (100 ml) was treated with sodium borohydride (0.3 g) and the mixture stirred overnight. Solvent was removed at reduced pressure the residue dissolved in ethyl acetate and washed with water and brine. The organic phase was dried (Na$_2$SO$_4$) solvent removed at reduced pressure and the residue triturated with diethyl ether to give the title compound (0.06 g) as a colourless solid. $^1$H NMR δ: 1.69 (2H, m), 1.87 (2H, m), 2.63 (3H, s), 2.67 (2H, m), 4.53 (1H, m), 5.01 (1H, d), 7.23–7.35 (3H, m), 7.79 (1H, dd), 8.29 (1H, dd), 8.36 (1H, s), 8.89 (1H, m), 9.90 (1H, s), 9.93 (1H, s). m/z (API$^+$): 349 (MH$^+$).

EXAMPLE 5

1-(3-Acetyl-4-methoxyphenyl)-3-(2-methyl-[1,5]-naphthyridin-4-yl)urea

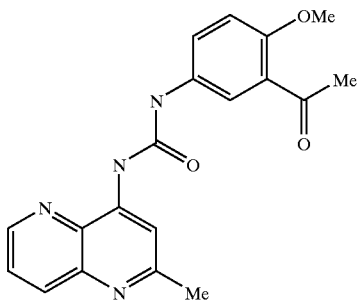

3-Acetyl-4-methoxybenzoic acid (0.082 g) in toluene (4 ml) was treated with triethylamine (0.176 ml) and subsequently with diphenylphosphoryl azide (0.092 ml). The mixture was stirred for 16 h at room temperature, D2 (0.067 g) added and the mixture heated to reflux for 4 h. After cooling to room temperature solvent was removed at reduced pressure and the residue column chromatographed (silica gel, 0–10% methanol in DCM containing 1% ammonia) to give the title compound (0.03 g) as a colourless solid. H NMR δ: 2.55 (3H, s), 2.63 (3H, s), 3.89 (3H, s), 7.18 (1H, d), 7.68 (1H, dd), 7.77–7.83 (2H, m), 8.28 (1H, dd), 8.34 (1H, s), 8.89 (1H, m), 9.85 (1H, s), 10.03 (1H, s). m/z (API$^+$): 351 (MH$^+$).

EXAMPLE 6

1-(3-Butyryl-4-methoxyphenyl)-3-(2-methyl-[1,5]-naphthyridin-4-yl)urea

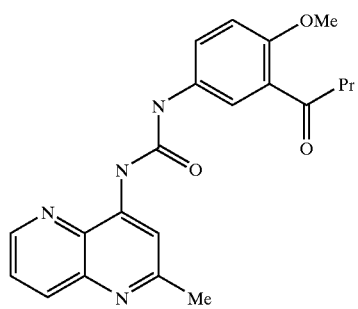

The title compound (0.075 g) was prepared from compound D2 (0.08 g) and 3-butyryl-4-methoxybenzoic acid (0.111 g) according to the method of Example 5. $^1$H NMR δ: 0.91 (3H, t), 1.53–1.68 (2H, m), 2.63 (3H, s), 2.91 (2H, t), 3.87 (3H, s), 7.15 (1H, d), 7.64 (1H, dd), 7.71 (1H, d), 7.80 (1H, dd), 8.28 (1H, dd), 8.34 (1H, s), 8.89 (1H, m), 9.85 (1H, s), 10.03 (1H, s). m/z (API$^+$): 379 (MH$^+$).

EXAMPLES 7–15

Were prepared according to a standard method from the appropriate carboxylic acid and 4-amino-2-methyl-1,5-naphthyridine as illustrated by Example 5, or from the appropriate aniline and 4-amino-2-methyl-1,5-naphthyridine as illustrated by Example 1.

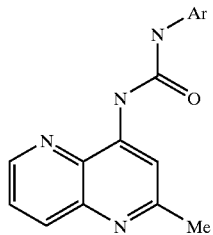

| Example | Precursor | Method | Ar | Yield | m/z |
|---|---|---|---|---|---|
| 7 | acid | E.g. 5 | 3-COMe, 4-Cl—C$_6$H$_3$ | 49% | MH$^+$ 355 |
| 8 | acid | E.g. 5 | 3-Cl, 4-OMe—C$_6$H$_3$ | 61% | MH$^+$ 343 |
| 9 | acid | E.g. 5 | | 6% | MH$^+$ 334 |
| 10 | acid | E.g. 5 | 3-Cl, 4-OS(O)$_2$Me—C$_6$H$_3$ | 52% | MH$^+$ 407 |
| 11 | acid | E.g. 5 | 3-Cl, 4-O(CH$_2$)$_2$OMe—C$_6$H$_3$ | 30% | MH$^+$ 387, 389 |
| 12 | aniline | E.g. 1 | 4-OMe, 3-CONHEt—C$_6$H$_3$ | 39% | MH$^+$ 380 |
| 13 | aniline | E.g. 1 | 4-COEt—C$_6$H$_4$ | 67% | MH$^+$ 335 |
| 14 | aniline | E.g. 1 | 4-[C(Me)$_2$OH]—C$_6$H$_4$ | 30% | MH$^+$ 337 |
| 15 | aniline | E.g. 1 | 4-COMe—C$_6$H$_4$ | 13% | MH$^+$ 321 |

$^1$H NMR spectra were consistent with the structures given in the table.

EXAMPLES 16–17

Were prepared according to a standard method from the appropriate ketone as illustrated by Example 4.

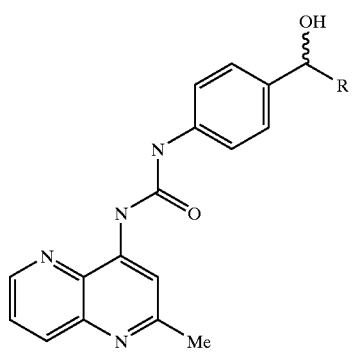

| Example No. | R | Yield | m/z |
|---|---|---|---|
| 16 | Me | 53% | MH$^+$ 323 |
| 17 | Et | 93% | MH$^+$ 337 |

$^1$H NMR spectra were consistent with the structures given in the table.

EXAMPLES 18–25

Were prepared by a standard method illustrated below for Example 18, using an appropriate and the carboxylic acid D4.

D4 (0.058 g) in DMF (3 ml) was treated with diisopropylethylamine (0.08 ml), O-(7-azabenzotriazol-1-yl)-1,1,3,3-tetramethyluronium hexafluorophosphate (HATU) (0.057 g) and butylamine (0.022 g) and shaken for 16 h. The reaction mixture was diluted with water, chilled and the precipitated solid collected by filtration, washed with water and diethyl ether and dried to give the title compound (0.03 g). Exceptionally the reaction mixture from Example 21 was diluted with water and extracted with ethyl acetate. The organic phase was washed with water, dried (Na$_2$SO$_4$) and solvent removed at reduced pressure to give Example 21 after trituration with water.

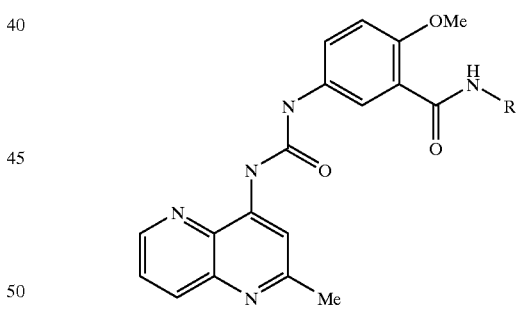

| Example No. | R | Yield | m/z |
|---|---|---|---|
| 18 | n-Butyl | 66% | MH$^+$ 408 |
| 19 | CH$_2$C(:CH$_2$)Me | 66% | MH$^+$ 406 |
| 20 | CH$_2$-(2-thienyl) | 60% | MH$^+$ 448 |
| 21 | cyclopropyl | 25% | MH$^+$ 392 |
| 22 | n-propyl | 68% | MH$^+$ 394 |
| 23 | CH$_2$C$_6$H$_5$ | 68% | MH$^+$ 442 |
| 24 | CH$_2$CH$_2$OMe | 66% | MH$^+$ 410 |
| 25 | CH$_2$C$_6$H$_4$-3-OMe | 59% | MH$^+$ 472 |

$^1$H NMR spectra were consistent with the structures given in the table.

EXAMPLES 26–28

Were prepared by a standard method illustrated below as Methods A and B for Examples 26 and 28 respectively, using an appropriate isocyanate and 4-amino-2-methyl-1,5-naphthyridine.

Method A: D2 (0.08 g) was dissolved in DMF containing sodium hydride (60% in oil 0.03 g). The mixture was stirred for 90 min then treated with 4-isocyanate-benzoic acid ethyl ester (0.096 g) and stirred for a further 3 h. The mixture was diluted with water (75 ml), the aqueous phase extracted with ethyl acetate (×2), the combined organic phase washed with water, dried (MgSO$_4$) and solvent removed at reduced pressure. The residue was triturated with diethyl ether to give the compound of Example 26 (0.10 g) as an off-white solid.

Method B: D2 (0.16 g) in toluene (15 ml) was treated with (4-isocyanatophenyl)-dimethylamine (0.16 g) in DCM (5 ml), stirred for 2 h, heated at 60° C. for 2 h and at 100° C. for 16 h. Solvent was removed at reduced pressure and the residue column chromatographed (silicaa gel, 0–5% methanol/diethyl ether) to give after conversion to the hydrochloride salt the compound of Example 28 (0.20 g) as a colourless solid.

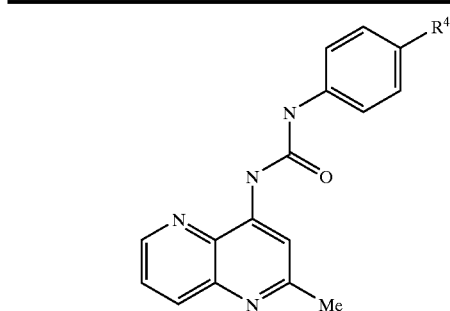

| Example No. | Method | R$^4$ | Yield | m/z |
|---|---|---|---|---|
| 26 | A | CO$_2$Et | 58% | MH$^+$ 351 |
| 27 | A | SMe | 68% | MH$^+$ 325 |
| 28 | B | NMe$_2$ | 51% | MH$^+$ 322 |

$^1$H NMR spectra were consistent with the structures given in the table.

EXAMPLE 29

N-Furan-2-ylmethyl-2-methoxy-5-[3-(2-methyl-[1,5]naphthyridin-4-yl)-ureido]-benzamide

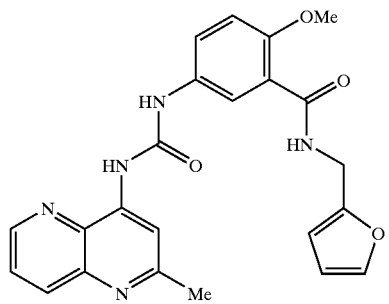

The title compound (0.05 g) was prepared from acid D4 (0.058 g) and furfurylamine (0.029 g) according to the method of Example 18. $^1$H NMR δ: 2.63 (3H, s), 3.88 (3H, s), 4.50 (2H, d, J=5.8 Hz), 6.28 (1H, d, J=3.1 Hz), 6.41 (1H, m), 7.14 (1H, d, J=9.0 Hz), 7.59 (1H, m), 7.68 (1H, dd, J=2.8, 8.9 Hz), 7.80 (1H, m), 7.89 (1H, d, J=2.8 Hz), 8.28 (1H, dd, J=1.5, 8.5 Hz), 8.35 (1H, s), 8.64 (1H, t, J=5.8 Hz), 8.88 (1H, m), 9.85 (1H, s), 10.03 (1H, s). m/z (API$^+$): 432 (MH$^+$).

EXAMPLE 30

1-(2-Cyclopropylmethyl-4-methyl-1-oxo-1,2-dihydro-isoquinolin-7-yl)-3-(2-methyl-[1,5]naphthyridin-4-yl)urea

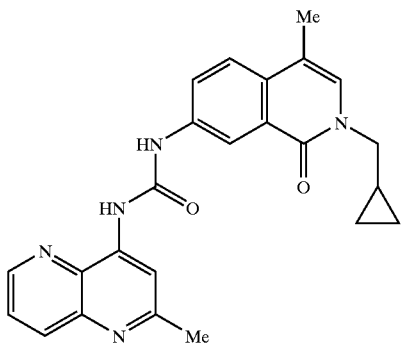

The title compound (0.025 g) was prepared was prepared from D5 (0.114 g) and D2 (0.08 g) according to the method of Example 1. $^1$H NMR δ: 0.38–0.53 (4H, m), 1.25 (1H, m), 2.24 (3H, s), 2.66 (3H, s), 3.79 (2H, d, J=7.1 Hz), 7.27 (1H, s), 7.67 (1H, d, J=8.7 Hz), 7.79 (1H, m), 7.90 (1H, dd, J=2.3, 8.8 Hz), 8.30 (1H, dd, J=1.4, 8.4 Hz), 8.40 (1H, s), 8.50 (1H, d, J=2.3 Hz), 8.91 (1H, m), 9.96 (1H, s), 10.37 (1H, s). m/z (API$^+$): 414 (MH$^+$).

EXAMPLE 31

1-[3-((E)-3-Furan-2-yl-allanoyl)-4-methoxy-phenyl]-3-(2-methyl-[1,5]naphthyridin-4-yl)-urea

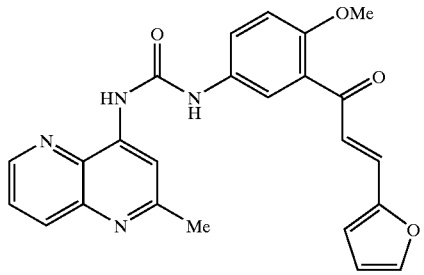

The title compound (0.02 g) was prepared from compounds D2 (0.02 g) and D7 (0.02 g) according to the method of Example 5. $^1$H NMR δ: 2.70 (3H, s), 3.88 (3H, s), 6.45 (1H, m), 6.54 (1H, m), 6.99 (1H, d, J=8.8 Hz), 7.35 15.6 Hz), 7.46–7.53 (3H, m), 7.59 (1H, d, J=2.8 Hz), 7.94 (1H, dd, J=2.8, 5.5 Hz), 8.21 (1 H, dd, J=1.2, 8.4 Hz), 8.38 (1H, s), 8.50 (1H, m), 8.71 (1H, s), 9.59 (1H, s). m/z (API$^+$): 429 (MH$^+$).

Determination of Orexin-1 Receptor Antagonist Activity

The orexin-1 receptor antagonist activity of the compounds of formula (I) was determined in accordance with the following experimental method.

EXPERIMENTAL METHOD

HEK293 cells expressing the human orexin-1 receptor were grown in cell medium (MEM medium with Earl's salts) containing 2 mM L-Glutamine, 0.4 mg/mL G418

Sulfate from GIBCO BRL and 10% heat inactivated fetal calf serum from Gibco BRL. The cells were seeded at 20,000 cells/100 µl/well into 96-well black clear bottom sterile plates from Costar which had been pre-coated with 10 µg/well of poly-L-lysine from SIGMA. The seeded plates were incubated overnight at 37° C. in 5% $CO_2$.

Agonists were prepared as 1 mM stocks in water:DMSO (1:1). $EC_{50}$ values (the concentration required to produce 50% maximal response) were estimated using 11×half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist $IC_{50}$ values (the concentration of compound needed to inhibit 50% of the agonist response) were determined against 3.0 nM human orexin-A using 11×half log unit dilutions in Tyrode's buffer containing 10% DMSO and probenecid. On the day of assay 50 µl of cell medium containing probenecid (Sigma) and Fluo3AM (Texas Fluorescence Laboratories) was added (Quadra, Tomtec) to each well to give final concentrations of 2.5 mM and 4 µM, respectively. The 96-well plates were incubated for 90 min at 37° C. in 5% $CO^2$. The loading solution containing dye was then aspirated and cells were washed with 4×150 µl Tyrode's buffer containing probenecid and 0.1% gelatin (Denley Cell Wash). The volume of buffer left in each well was 125 µl. Antagonist or buffer (25 µl) was added (Quadra) the cell plates gently shaken and incubated at 37° C. in 5% $CO_2$ for 30 min. Cell plates were then transferred to the Fluorescent Imaging Plate Reader (FLIPR, Molecular Devices) instrument and maintained at 37° C. in humidified air. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 sec (during continuous reading). From each well, peak fluorescence was determined over the whole assay period and the mean of readings 1–19 inclusive was subtracted from this figure. The peak increase in fluorescence was plotted against compound concentration and iteratively curve fitted using a four parameter logistic fit (*TiPS*, 1995, 16, 413–417) to generate a concentration effect value. Antagonist $K_b$ values were calculated using the equation:

$$K_b = IC_{50}/(1+([3]/EC_{50}])$$

where $EC_{50}$ was the potency of human orexin-A determined in the assay (in nM terms) and $IC_{50}$ is expressed in molar terms.

As an illustration of the activity of the compounds of formula (I), the compound of example 2 had a pkb>7.5 in this assay.

What is claimed is:

1. A compound selected from the following:

2-methoxy-5-[3-(2-methyl-[1,5]-naphthyridin4-yl) ureido]benzoic acid methyl ester;

N-cyclopropylmethyl-2-methoxy-5-[3-(2-methyl-[1,5]-naphthyridin4-yl)ureido]benzamide hydrochloride;

1-(2-methyl-[1,5]-naphthyridin-4-yl)-3-(5-oxo-5,6,7,8-tetrahydronaphthalen-2-yl)urea;

1-(5-hydroxy-5,6,7,8-tetrahydronaphthalen-2-yl)-3-(2-methyl-[1,5]-naphthyridin4-yl)urea;

1-(3-acetyl-4-methoxyphenyl)-3-(2-methyl-[1,5]-naphthyridin-4-yl)urea;

1-(3-butyryl-4-methoxyphenyl)-3-(2-methyl-[1,5]-naphthyridin-4-yl)urea;

1-(3-acetyl-4-chloro-phenyl)-3-(2-methyl-[1,5] naphthyridin-4-yl)-urea;

1-(3-chloro-4-methoxy-phenyl)-3-(2-methyl-[1,5] naphthyridin-4-yl)-urea;

1-(2-methyl-benzoxazol-6-yl)-3-(2-methyl-[1,5] naphthyridin-4-yl)-urea;

methanesulfonic acid 2-chloro-4-[3-(2-methyl-[1,5] naphthyridin-4-yl)-ureido]-phenyl ester;

1-[3-chloro-4-(2-methoxy-ethoxy)-phenyl]-3-(2-methyl-[1,5]naphthyridin-4-yl)-urea;

N-ethyl-2-methoxy-5-[3-(2-methyl-[1,5]naphthyridin-4-yl)-ureido]-benzamide;

1-(2-methyl-[1,5]naphthyridin-4-yl)-3-(4-propionyl-phenyl)-urea;

1-[4-(1-hydroxy-1-methyl-ethyl)-phenyl]-3-(2-methyl-[1,5]naphthyridin-4-yl)-urea;

1-(4-acetyl-phenyl)-3-(2-methyl-[1,5]naphthyridin-4-yl)-urea;

1-[4-(1-hydroxy-ethyl)-phenyl]-3-(2-methyl-[1,5] naphthyridin-4-yl)-urea;

1-[4-(1-hydroxy-propyl)-phenyl]-3-(2-methyl-[1,5] naphthyridin-4-yl)-urea;

N-butyl-2-methoxy-5-[3-(2-methyl-[1,5]naphthyridin-4-yl)-ureido]-benzamide;

2-methoxy-N-(2-methyl-alkyl)-5-[3-(2-methyl-[1,5] naphthyridin-4-yl)-ureido]-benzamide;

2-methoxy-5-[3-(2-methyl-[1,5]naphthyridin-4-yl)-ureido]-N-thiophen-2-ylmethyl-benzamide;

N-cyclopropyl-2-methoxy-5-[3-(2-methyl-[1,5] naphthyridin-4-yl)-ureido]-benzamide;

2-methoxy-5-[3-(2-methyl-[1,5]naphthyridin-4-yl)-ureido]-N-propyl-benzamide;

N-benzyl-2-methoxy-5-[3-(2-methyl-[1,5]naphthyridin-4-yl)-ureido]-benzamide;

2-methoxy-N-(2-methoxy-ethyl)-5-[3-(2-methyl-[1,5] naphthyridin-4-yl)-ureido]-benzamide;

2-methoxy-N-(3-methoxy-benzyl)-5-[3-(2-methyl-[1,5] naphthyridin-4-yl)-ureido]-benzamide;

4-[3-(2-methyl-[1,5]naphthyridin-4-yl)-ureido]-benzoic acid ethyl ester;

1-(2-methyl-[1,5]naphthyridin-4-yl)-3-(4-methylsulfanyl-phenyl)-urea;

1-(4-dimethylamino-phenyl)-3-(2-methyl-[1,5] naphthyridin-4-yl)-urea;

N-furan-2-ylmethyl-2-methoxy-5-[3-(2-methyl-[1,5] naphthyridin-4-yl)-ureido]-benzamide;

1-(2-cyclopropylmethyl-4-methyl-1-oxo-1,2-dihydro-isoquinolin-7-yl)-3-(2-methyl-[1,5]naphthyridin-4-yl) urea; or 1-[3-((E)-3-furan-2-yl-allanoyl)-4-methoxy-phenyl]-3-(2-methyl-[1,5]naphthyridin-4-yl)-urea;

or a pharmaceutically acceptable salt thereof.

2. A pharmaceutical composition comprising the compound according to claim 1, or a pharmaceutically acceptable salt thereof, and a pharmaceutically acceptable carrier.

3. A method of treating a disease or disorder where an antagonist of a human orexin receptor is required, which comprises administering to a subject in need thereof an orexin receptor antagonizing of the compound according to claim 1 or a pharmaceutically acceptable salt thereof.

* * * * *